(12) United States Patent
Abdel-Rahman

(10) Patent No.: US 8,590,168 B2
(45) Date of Patent: Nov. 26, 2013

(54) PEDIATRIC WEIGHT ESTIMATE DEVICE AND METHOD

(75) Inventor: Susan M. Abdel-Rahman, Kansas City, MO (US)

(73) Assignee: The Childrens' Mercy Hospital, Kansas City, MO (US)

( * ) Notice: Subject to any disclaimer, the term of this patent is extended or adjusted under 35 U.S.C. 154(b) by 266 days.

(21) Appl. No.: 13/271,112

(22) Filed: Oct. 11, 2011

(65) Prior Publication Data

US 2012/0085277 A1    Apr. 12, 2012

Related U.S. Application Data

(60) Provisional application No. 61/392,008, filed on Oct. 11, 2010.

(51) Int. Cl.
*G01B 5/02*     (2006.01)

(52) U.S. Cl.
USPC ............................................. 33/512; 33/755

(58) Field of Classification Search
USPC .................................... 33/511, 512, 755, 759
See application file for complete search history.

(56) References Cited

U.S. PATENT DOCUMENTS

| | | | | |
|---|---|---|---|---|
| 3,336,674 A * | 8/1967 | Gratopp et al. | .................. | 33/759 |
| 4,688,653 A * | 8/1987 | Ruble | .............. | 33/759 |
| 4,713,888 A * | 12/1987 | Broselow | ......... | 33/512 |
| 4,823,469 A * | 4/1989 | Broselow | ......... | 33/760 |
| D357,425 S * | 4/1995 | Youdelman | ......... | D10/71 |
| 5,813,132 A * | 9/1998 | Bodkin, Sr. | ......... | 33/759 |
| 6,314,654 B1 * | 11/2001 | Morissette | ......... | 33/511 |
| D460,366 S * | 7/2002 | Winter | ............ | D10/70 |
| 6,820,033 B1 * | 11/2004 | Hapgood et al. | ......... | 33/511 |
| 7,249,423 B2 * | 7/2007 | Sieber | .............. | 33/512 |
| 7,685,727 B2 * | 3/2010 | Sieber | .............. | 33/512 |
| 7,905,028 B2 * | 3/2011 | Sieber | .............. | 33/512 |
| 2002/0046471 A1 * | 4/2002 | Skidmore | ......... | 33/511 |
| 2006/0265892 A1 * | 11/2006 | Sieber | .............. | 33/512 |
| 2008/0184575 A1 * | 8/2008 | Sieber | .............. | 33/512 |
| 2009/0094138 A1 | 4/2009 | Sweitzer | | |
| 2009/0193675 A1 | 8/2009 | Sieber | | |
| 2012/0085277 A1 * | 4/2012 | Abdel-Rahman | ............ | 116/201 |

* cited by examiner

*Primary Examiner* — Yaritza Guadalupe-McCall

(74) *Attorney, Agent, or Firm* — Tracy S. Truitt; Polsinelli PC

(57) ABSTRACT

The present invention is directed towards a device, method of using a device, and a method of making a device for predicting weight and/or the appropriate dose of a medication and/or degree of some other medical intervention in a child. The device includes one or more strips for taking a girth and a length measurement from an individual. The method includes adding or otherwise combining a value given by a girth measurement and a value given by a length measurement together to estimate the weight of the individual.

30 Claims, 8 Drawing Sheets

FIG. 2

| Method | Basis for weight | Lower age limit | Upper age limit | Length restrictions | % Predicted[a] | Slope [95% CI] | Intercept | r² |
|---|---|---|---|---|---|---|---|---|
| Mercy method | MUAC & HL | 2 mo | 16 yr | none | 100 | 0.965 [0.958, 0.971] | 0.9 | 0.98 |
| APLS | age | 1 yr | 10 yr | none | 52.3 | 0.425 [0.407, 0.443] | 8.4 | 0.69 |
| ARC | age | 1 yr | none | none | 90.4 | 0.508 [0.494, 0.523] | 9.8 | 0.74 |
| Argall formula | age | 1 yr | 10 yr | none | 52.3 | 0.638 [0.611, 0.664] | 6.6 | 0.69 |
| Best Guess | age | none | 14 yr | none | 80.6 | 0.666 [0.647, 0.684] | 8.0 | 0.76 |
| Broselow | TBL | none | none | 46-143 cm | 62.6 | 0.727 [0.710, 0.744] | 3.8 | 0.86 |
| Cattermole | MUAC | 6 | 11 | none | 27.3 | 0.866 [0.837, 0.895] | 5.3 | 0.87 |
| Leffler | age | none | 10 yr | none | 61.9 | 0.513 [0.495, 0.531] | 7.5 | 0.72 |
| Luscombe & Owens | age | 1 yr | 10 yr | none | 52.3 | 0.638 [0.611, 0.664] | 7.6 | 0.69 |
| Nelson | age | 3 mo | 12 yr | none | 72.2 | 0.642 [0.623, 0.661] | 6.1 | 0.76 |
| Shann | age | 1 yr | none | none | 90.4 | 0.425 [0.413, 0.437] | 11.8 | 0.73 |
| Theron | age | 1 yr | 10 yr | none | 52.3 | 0.960 [0.921, 0.999] | 3.1 | 0.70 |
| Traub-Johnson | age & TBL | 1 yr | 18 yr | none | 90.4 | 0.703 [0.687, 0.719] | 7.1 | 0.81 |
| Traub-Kichen | age & TBL | 1 yr | 17 yr | >74 cm | 90.1 | 0.629 [0.614, 0.643] | 8.4 | 0.81 |

APLS- Advanced Pediatric Life Support, ARC- Australian Resuscitation Council, TBL- total body length, MUAC- mid-upper arm circumference, HL- humeral length
[a] percentage of the 1,938 children in the validation set for whom a weight would be predicted using this method

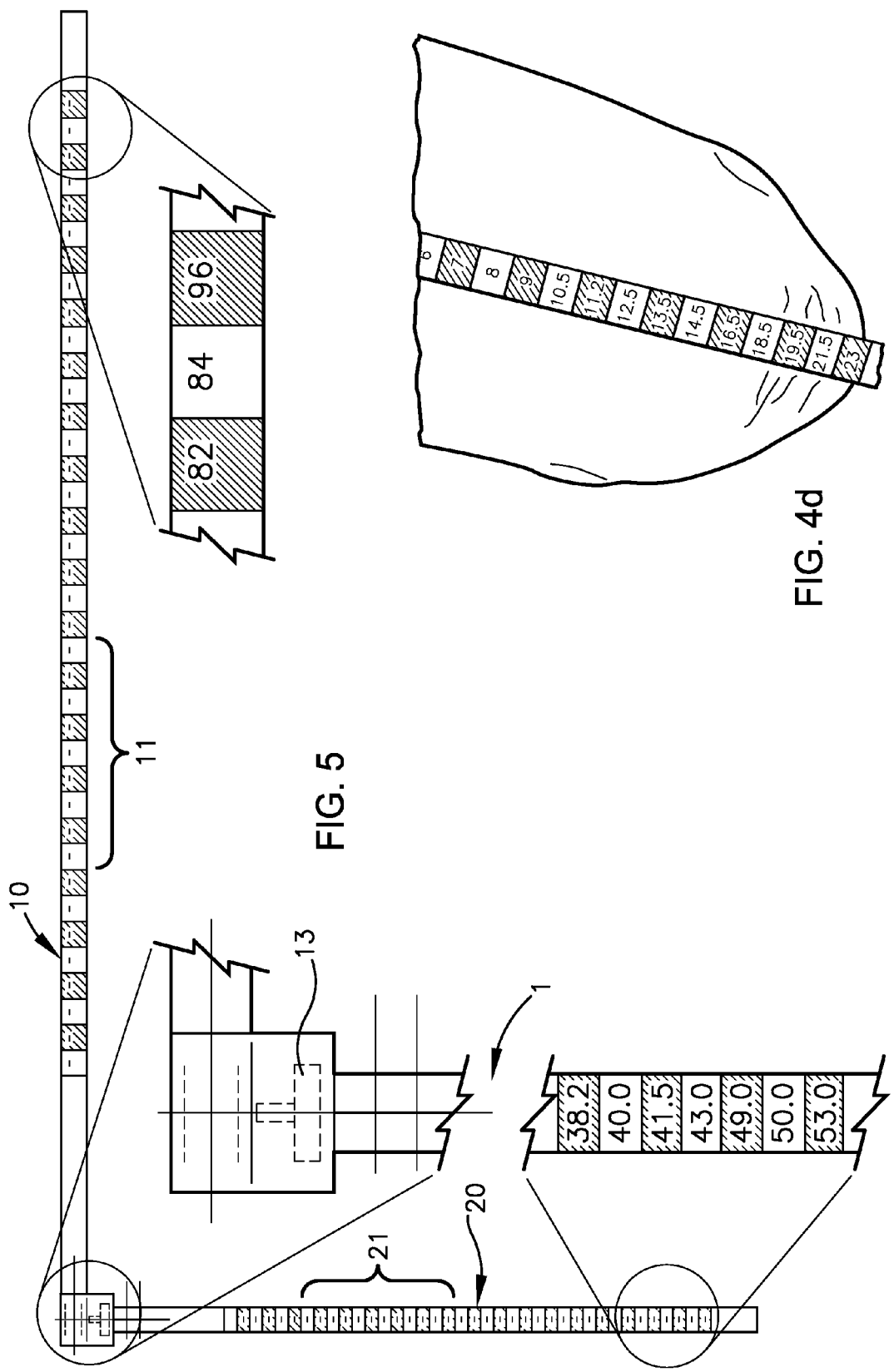

FIG. 8

| Method | MPE[a] (%) | ME[a] (kg) | RMSE[a] (kg) | percentage in agreement within: | | | | | | |
|---|---|---|---|---|---|---|---|---|---|---|
| | | | | 10% | 20 | 30 | 40 | 50 | >50 | no call |
| Mercy method | -0.46 ± 8.38 | -0.40 | 3.65 | 78.6 | 98.0 | 99.6 | 99.9 | 100 | | |
| APLS | -14.88 ± 17.17 | -4.87 | 8.97 | 17.8 | 33.2 | 42.5 | 47.8 | 50.5 | 52.3 | 100 |
| ARC | -16.84 ± 19.04 | -9.49 | 16.96 | 27.5 | 51.0 | 68.2 | 78.7 | 86.1 | 90.4 | 100 |
| Argall formula | -4.55 ± 20.50 | -1.78 | 6.84 | 19.8 | 34.4 | 44.6 | 49.7 | 51.2 | 52.3 | 100 |
| Best Guess | 0.98 ± 21.69[b] | -1.65 | 9.96 | 31.2 | 54.0 | 68.2 | 74.9 | 78.5 | 80.7 | 100 |
| Broselow | -6.05 ± 12.28 | -1.85 | 4.88 | 37.4 | 53.9 | 59.8 | 61.9 | 62.5 | 62.6 | 100 |
| Cattermole | 3.51 ± 12.07 | 0.73 | 3.42 | 15.5 | 23.9 | 26.6 | 27.0 | 27.1 | 27.1 | 100 |
| Leffler | -5.52 ± 19.59 | -2.61 | 7.44 | 24.8 | 42.9 | 53.3 | 58.6 | 60.7 | 61.9 | 100 |
| Luscombe & Owens | 0.82 ± 20.83[c] | -0.78[d] | 6.65 | 20.2 | 35.9 | 44.9 | 49.2 | 51.1 | 52.3 | 100 |
| Nelson | -7.69 ± 19.49 | -3.19 | 9.33 | 25.9 | 49.4 | 61.7 | 67.8 | 70.7 | 72.2 | 100 |
| Shann | -17.38 ± 20.94 | -10.88 | 18.78 | 26.3 | 48.6 | 64.0 | 75.7 | 84.1 | 90.4 | 100 |
| Theron | 9.64 ± 26.44 | 2.23 | 7.720 | 19.6 | 33.4 | 41.7 | 45.4 | 47.8 | 52.3 | 100 |
| Traub-Johnson | -7.13 ± 15.81 | -4.52 | 11.93 | 45.2 | 69.3 | 81.7 | 87.3 | 90.0 | 90.4 | 100 |
| Traub-Kichen | -9.48 ± 15.90 | -6.18 | 13.23 | 45.3 | 67.8 | 79.0 | 85.6 | 89.2 | 90.1 | 100 |

MPE- mean percentage error (± standard deviation), ME, mean error, RMSE- root mean square error
[a] $p<0.001$ between Mercy and all other methods except where designated, [b] $p=0.03$ vs. Mercy, [c] $p=0.04$ vs. Mercy, [d] $p=0.002$ vs. Mercy

PEDIATRIC WEIGHT ESTIMATE DEVICE AND METHOD

RELATED APPLICATIONS

This application relates to and claims priority to U.S. Provisional Patent Application No. 61/392,008, which was filed Oct. 11, 2010, the teachings and contents of which are incorporated herein by reference in its entirety.

BACKGROUND

In pediatric medicine, almost every intervention is based on the weight of the patient. Medication doses are based on weight, resuscitation fluid volumes are based on weight, shock voltages administered during cardio-respiratory arrest are based on weight and breathing tubes are sized by weight. Yet, there are a number of circumstances where the weight of a child is unavailable. In developing countries, many medical clinics lack suitable scales that can be used to accurately obtain the weight of an infant or child. In developed countries, accurate estimates of a child's weight are rarely available during emergency/trauma situations both "in the field" and in the emergency room. In some settings, such as intensive care nurseries, scales are available but obtaining an accurate weight is impaired by the presence of external hoses, tubing and other medical equipment. Each of these scenarios pose a significant challenge to providing age-appropriate treatment including drug therapy with weight-based drug dosing which is recognized as the most accurate approach to delivering medicines.

Current strategies aimed at addressing weight estimation rely on; 1) age alone, 2) length alone, (e.g. total body length or height), or 3) age and length in some combination. Age based strategies fail to consider that two children of the same age may exhibit very different body compositions. Length based strategies do not take into consideration that two children of the same height may demonstrate markedly discrepant weights if one is malnourished/underweight or overweight/obese. Finally, age and length based strategies do not correct for the fact that weight increases disproportionately with height as children mature into adulthood. Importantly, all of the currently available weight estimation strategies perform well in only a small subset of children (i.e. those within normal limits of height and weight for age) deriving from the population in whom the method was developed.

What is needed in the art is an improved device and method for estimating the weight of a child or the appropriate dose of a medication that can easily be used in a clinical setting with greater accuracy than previous devices and methods. Further, what is needed is a method of making such a device based on creating a scale of numbers, indicia, or symbols that correspond to the weight of a child and/or dose of medication required, and/or degree of some other medical intervention.

SUMMARY OF THE INVENTION

The present invention overcomes the problems inherent in the prior art and provides devices and methods for easily estimating the weight of a child or the appropriate dose of a medication for a child. Additionally, a method for designing a weight estimating device is also disclosed.

Advantageously, the device and method of the present invention incorporates surrogates for both stature and body habitus ("physique") into a weight estimation strategy that performs robustly independently of age, weight, gender, and geographic origin over a large range of variables varying independently or together. The present invention was developed on the premise that weight is influenced by both height and girth and that the incorporation of measurements (e.g. height, armspan) or surrogate measurements (e.g. humeral length, ulnar length, tibial length, middle-upper arm circumference, thigh circumference, neck circumference, abdominal circumference) for both of these parameters introduces less error in the predicted weight than would be introduced if relying on either a height measurement (or surrogate) or girth measurement (or surrogate) alone. The present invention advantageously simplifies the measurement process so that two (direct or surrogate) measurements can be made simultaneously or in series and the weight subsequently read directly from the device (as opposed to consulting a separate table or chart to see how the two measurements combine to yield the predicted weight).

Preferably, the device consists of one or more strips each containing an indication or indicia for use in measuring one or more body parts of a child in order to estimate the child's weight or determine the appropriate dose of medication. In one embodiment, the device consists of two perpendicular strips that are arranged such that a user could simultaneously take a length measurement and a girth measurement. Preferably, the strips are oriented such that there is a horizontal strip and a vertical strip, where those orientations are relative to an individual standing upright. The horizontal strip is preferably used for taking a girth measurement and the vertical strip is preferably used for taking a length measurement. In another embodiment, the device consists of a singular strip with the measurement for girth printed on one side and the measurement for length printed on the opposite side. The embodiment of the two sided strip is preferably oriented such that a girth measurement can be taken using one side of the strip and a length measurement can be taken using the other side of the strip.

The one or more strips that are part of the device can be made from any flexible material that is able to be printed upon and used in measuring the length or circumference of a body part. Preferably, the strips will also be non-deformable such that any scale of indicia printed thereon will not be deformed (i.e., it will not be distorted) during use, shipping, or storage of the strips. Preferably, the material for the strips can be selected from, but is not limited to, ribbon, plastic compositions, waxed paper, paper, metal, silicon, natural and man-made fibers, and the like. In a most preferred embodiment the one or more strips are made of commonly available fibers, such as paper.

Preferably, a scale of indicia is printed on the strip. The printing can either be on one or both sides of the strip. The indicia can include numbers, letters, symbols, colors, or other indicia. In a preferred embodiment, numbers are printed on the strip. The numbers printed on the strip preferably correspond with a fraction of the child's weight. Weight can be in pounds or kilograms, but preferably, weight is in kilograms. In a preferred embodiment, there are two strips on the device, each printed with a separate scale corresponding to the length or girth measurement of a body part such that one must simply add the values corresponding to the partial weight assigned by measurement of the girth and length of the body part in order to estimate the weight of the child.

In an alternate embodiment, the printing on the strip is a color, symbol, letter, or other non-numeric indicia. The color and/or symbol preferably correspond to a reference table. In one embodiment with two scales, one scale will be printed with colors and one scale will be printed with symbols. By measuring the girth and length, one will come up with a color/symbol combination. The reference table preferably correlates the color/symbol combination with the appropriate dose of medication for the child. It can be appreciated that any combination of two or more colors, symbols, letters, or indicia can be used for this embodiment of the present invention, such that a combination of colors, symbols, letters or indicia corresponds to a table entry indicating a dose of medication. Additionally, it can be appreciated that the scale will be different depending on the medication.

The device can be used to take one, two, three, four, or more measurements. In a preferred embodiment, two measurements are taken. Preferably, a length measurement and a girth measurement are taken. In a preferred embodiment, the device is the appropriate size for measuring a body part. Preferably, the body part measured is the arm, leg or neck, however, it can be appreciated that there are several other body measurements that could be used, including, but not limited to the shoulders, back, abdomen, etc. Any bone within the body part can be measured for length and the circumference of any body part can be measured for girth. Specifically, bones within body parts may be measured. These bones are preferably selected from, but are not limited to, the humerus, tibia, ulna, fibula, radius, or any other long bone in the body. The length measurement taken is preferably either the length from the distal to proximal end of the bone or the length from the mid-point to the end of the bone. In a most preferred embodiment, the length is one half of a long bone. The girth measurement taken is preferably the circumference of the body part taken from the middle of the body part whose length is being measured. In a most preferred embodiment, the arm is measured, more preferably, the length of half of the humerus is measured for length and the circumference of the upper arm in the middle of the upper arm is measured for girth.

In an embodiment where the device comprises two strips, it is preferred that the two strips are oriented perpendicular to one another such that there is a horizontal strip and a vertical strip, where those orientations are relative to an individual standing upright. The horizontal strip preferably measures the girth and is oriented such that it forms a circle or closed loop. Preferably, one end of the horizontal strip is slidably engaged with the other end of the strip. The vertical strip preferably measures the length and can be oriented below the horizontal strip and affixed to the horizontal strip perpendicularly to create a single device.

An alternate embodiment includes a device with a single strip, where one side of the strip is printed with a scale for measuring girth and the other side of the strip is printed with a scale for measuring length. Preferably, this device includes a single strip of material that is printed on both sides.

Another alternate embodiment includes a device of the present invention, as described above, wherein the indicia on either of the embodiments can be designed for specific dosages of specific medications. In such an embodiment, the indicia would directly relate to dosage amounts of specific medications. For example, the length and girth measurements may each relate to a scale designating dosage amounts (e.g. ml, mg, cc, IU, etc). The two measurements would be taken and the indicia corresponding to each measurement would be added together or otherwise combined to provide an actual dosing amount that was appropriate for the child being measured.

A method for determining the weight of a child is also disclosed. The method comprises taking one or more measurements from a child and determining the approximate weight of the child or the appropriate dose of medication for a child.

In a preferred embodiment, the method generally includes the steps of taking two measurements from one or more body parts of a child (each measurement yielding a partial weight or dose) and adding or otherwise combining the two measurements together to determine the weight of the child or the appropriate dose of medication for the child. Preferably, the measurements are taken from the arm or leg, however, it can be appreciated that there are several other body measurements that could be used, including, but not limited to the arm, leg, shoulders, back, neck, abdomen, etc. Further, any bone within the body part can be measured for length. Preferably, the length measurement is taken by measuring half the length of a long bone or the length of the bone from the proximal end to the distal end of the bone. Most preferably, the length is measured using half of the length of the bone. Preferably, girth is measured using the circumference of a body part. The bones within the body part(s) that can be used to measure length are preferably selected from, but are not limited to, the humerus, tibia, ulna, fibula, radius, or any long bone in the body. In a most preferred embodiment, the upper arm is measured, more preferably, the humerus is measured for length and the circumference of the center of the upper arm is measured for girth. In an alternate embodiment, the circumference of the neck is measured for girth and the length of a long bone in the body is used for the length measurement. In yet another alternate embodiment, the circumference of the upper leg is used for measuring girth and the length of the femur or half of the femur is used to measure length. In yet another embodiment, the girth measurement is taken from the midpoint of the calf and the length measurement is taken from the midpoint to the distal end of the tibia. It can be appreciated that the combination of any girth measurement and length measurement will work for purposes of the present invention.

Preferably, the method utilizes the device of the present invention. In an embodiment of the method where a device comprising two strips is used, each strip is printed with a separate scale corresponding to a partial weight assigned to the length measurement and a girth measurement. In this embodiment, the method includes taking a girth measurement and a length measurement and adding or otherwise combining the values corresponding to the measurements together in order to estimate or determine the weight of the child. In an alternate embodiment, the method utilizes a device comprising two strips where each is printed with a color or symbol. The color and/or symbol combination preferably corresponds to a reference table. Preferably, in an embodiment with two strips, one strip will be printed with colors and one strip will be printed with symbols. In this embodiment, the method comprises measuring the girth and length of one or more body parts and determining a color/symbol combination. The next step of the method includes correlating the color/symbol combination with a reference table to determine the appropriate dose of medication for the child. In an embodiment of the method where the device consists of a single strip that is printed on both sides, one side of the strip is used for taking a girth measurement and the other side of the strip is used for taking a length measurement. In this embodiment, each of the measurements will correspond to a different indicia scale on each respective side of the strip. The indicia or weight assigned to girth and length measurements are then added together or otherwise combined to determine the weight of the child.

A method for making the device of the present invention is also disclosed. The method includes the steps of obtaining one or more datasets correlating weight and length and girth measurements of body parts, using a mathematical equation to create one or more scales based on the one or more datasets that correlate length and girth measurements to weight, and printing one or more strips with the one or more scales and orienting the strips to create a device for estimating weight or dose. Preferably, this method results in the device of the present invention that is used according to the method of using the device disclosed herein.

The method generally includes obtaining one or more datasets and examining length (or a length surrogate) and girth (or a girth surrogate) against the median population weight for individuals with the same length/girth values. From this, a mathematical model, preferably, a mathematical function in two variables and with one or more empirically determined parameters or "constants", is developed which predicts weight.

Preferably, the method comprises obtaining two body measurements, one length (xi) and one girth (yi) and the corresponding weight (Wi) for each individual i in a large population, n, such as that reported in the CDC data. A function F is sought such that $F(xi,yi,a\_matrix)$ approximates Wi over that population. Preferably, "a" is a set of parameters (constants empirically determined as described below) whose values can be adjusted to optimize the fit (minimize the errors) between the measured weights Wi and the weights computed from F. The set of the "a" values, a_matrix, can be determined by nonlinear regression techniques.

Preferably, W varies smoothly with x and y, and for modest range of ages, for example 2 months to 16 years, F can be approximated as a polynomial in second order in x, y: $F(x,y, a\_matrix)=a00+a10*x+a20*x^2+a01*y+a02*y^2+a11*x*y$. Here "*" indicates multiplication and "^" indicates exponentiation, and 00, 10, 11, etc. are subscript labels. It can be appreciated that other functional forms are also possible. In order to produce the device of the present invention suitable for taking two body measurements simultaneously and reading off a predicted weight, the cross term (a11*x*y) was deleted and F was considered to be separable in the variables x and y. Considering F as separable in x and y somewhat degrades or weakens how well F can approximate the observed weights but has advantages for the overall method and device.

Preferably, in order to compensate for the absence of a cross term the search for a single global functional form F that fits the entire population at once was abandoned and, instead, a function u(x,b-vector) was found, for example by nonlinear regression, that approximates the weight at various x values without regard to the corresponding y values, and another function v(y,c-vector) that approximates, for example by nonlinear regression, the weight at various y values without regard to corresponding x values was found. Here, b-vector and c-vector were sets of parameters adjusted to optimize the respective fits. For example, in the same notation as above, u(x,b-vector) could take the form $b0+b1x+b2*x^2$, and correspondingly for v(y,c-vector).

Using the method of creating the device of the present invention, an individual's weight could in principle be crudely determined either by: 1) measuring that individual's x value and computing, or looking up in a table, or reading off a calibrated linear scale, u(x,b-vector), or by 2) measuring that individual's y value and computing, or looking up in a table, or reading off a calibrated linear scale, v(y,c-vector). That single-variable approach, although common in the prior art, is too crude to be useful over the desired wide ranges of x and y, and typically fails badly at the high or low end of the range of x or y, or of both. Thus, the method preferably includes retaining the separable approximation for the fitting function F, and utilizes a better approach than in the prior art by measuring both x and y for an individual, preferably simultaneously, and estimating the weight as the combination $W(x, y)=A\_sub\_x*u(x,b\text{-vector})+A\_sub\_y*v(y,c\text{-vector})$, where A_sub_x and A_sub_y are constants and u(x,b-vector) and v(y,c-vector) are determined as above. Those constants "A" are determined by a least-squares fit of W(x,y) to the given population of CDC data Wi(xi, yi). Since either u(x) or v(y) can crudely approximate weight by itself, it can be expected that A_sub_x and A_sub_y add to approximately 1.0 to avoid "double-counting".

The device and methods of the present invention are preferably made for children, but can also be used for adults. An embodiment created for an adult would simply use a different dataset(s) to determine a different scale of numbers and/or indicia corresponding to weight or dose. Further, the device and methods of the present invention can be customized to fit different populations of adults and children depending on different factors such as, but not limited to, geographic origin, age, ethnic background, nutritional status, and other social factors.

In preferred forms, the present invention provides a device for estimating weight in a child between the ages of 2 months to 16 years, wherein the device generally includes a flexible elongate strip having a front side and a back side. Preferably, each of the front side and the back side includes a scale of indicia thereon. Preferably, the scale of indicia on the front side provides a first value when the flexible elongate strip is used to measure the circumference of a body part and the scale of indicia on the back side provides a second value when the flexible elongate strip is used to measure at least a portion of the length of a body part. When the first value and the second value are added together, they accurately estimate the weight of the child. In some preferred forms, the scale of indicia for the front side is derived for a circumference measurement of a body part selected from the group consisting of the upper arm, neck, abdomen, and upper leg. In other preferred forms, the scale of indicia for the back side is derived for a length measurement of at least a portion of a body part selected from the group consisting of the humerus, ulna, tibia, and femur. In the embodiments used in the examples herein, the length measurement used is the humerus. Preferably, the body part used for the circumference measurement and the body part used for the length measurement are the same body part. However, the scales of indicia can be designed such that one body part can be measured for girth and another body part measured for length and accurate weights still be obtained. In preferred forms, the scale of indicia for the front side and the back side is in 1 cm or 0.5 cm gradations. One particularly preferred scale for measuring the circumference or girth of the middle of the upper arm (the midpoint of the humerus) has 1 cm gradations on the scale of indicia of 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively. One particularly preferred scale for measuring the length of half of the humerus has 1 cm gradations on the scale of indicia of 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively. Preferably, the indicia on each scale of indicia are in a form selected from the group consisting of numbers, letters, symbols, colors, and combinations thereof.

Another preferred device for estimating weight in a child between the ages of 2 months to 16 years generally includes a first flexible elongate strip having a front side including a scale of indicia thereon and a second flexible elongate strip having a front side including a scale of indicia thereon. Although they may be provided as separate strips, it is preferred that the first flexible elongate strip and the second flexible elongate strip are attached to one another and that the first elongate strip be slidably engaged between its two ends. In this preferred form, it is also preferred that the first flexible elongate strip be oriented perpendicularly to said second flexible elongate strip. The scale of indicia on the first flexible elongate strip is designed to provide a first value when used to measure the circumference of a body part and the scale of indicia on the second elongate strip is designed to provide a second value when used to measure at least a portion of the length of a body part. The first value and the second value are then combined or added together to estimate the weight of the child. In preferred forms, the scale of indicia for the first flexible elongate strip is derived for a circumference measurement of a body part selected from the group consisting of the upper arm, neck, abdomen, and upper leg. Similarly, in other preferred forms, the scale of indicia for the second flexible elongate strip is derived for a length measurement of at least a portion of a body part selected from the group consisting of the humerus, ulna, tibia, and femur. One preferred length measurement, and the one that is used in the Examples herein, is one half of the length of the humerus. On preferred circumference measurement, and the one that is used in the Examples herein, is taken at the midpoint of the humerus. Preferably, the scale of indicia for each of the first and second flexible elongate strips is in 1 cm and 0.5 cm gradations, respectively. Preferred gradations on the scale of indicia when the circumference of the midpoint of the humerus is measured by the first flexible elongate strip are 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively. When the half length of the humerus is used for the length measurement, the scale of indicia for said second flexible elongate strip are 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively. It is understood that each of the preferred gradations may vary if further data is developed that would cause the scales to change. However, at this point in time, it appears that these gradations are accurate for the populations described herein. Preferably, the indicia on each scale of indicia are in a form selected from the group consisting of numbers, letters, symbols, colors, and combinations thereof.

The present invention also provides a method of estimating the weight of a child between 2 months and 16 years of age. The method generally includes the steps of measuring the circumference of a first body part using a flexible elongate strip having a first scale of indicia thereon; measuring the length of at least a portion of a second body part using a flexible elongate strip having a second scale of indicia thereon; wherein the first scale of indicia provides a first value when used to measure the circumference of a body part and the second scale of indicia provides a second value when used to measure at least a portion of the length of a body part; and combining the first value and the second value to thereby estimate the weight of the child. In one form of the method, the first scale of indicia and the second scale of indicia are on opposing sides of said flexible elongate strip. In another form of the method, the first scale of indicia is on a first flexible elongate strip and the second scale of indicia is on a second flexible elongate strip. In forms using two strips, the first flexible elongate strip and the second flexible elongate strip are preferably attached to one another. Preferably, the horizontal strip used to measure circumference is looped such that one end of the strip is slidably engaged with the opposite end.

Additionally, it is preferred in this form to have the first flexible elongate strip be oriented perpendicularly to the second flexible elongate strip. In preferred forms, the first scale of indicia is derived for a circumference measurement of a body part selected from the group consisting of the upper arm, neck, abdomen, and upper leg. Similarly, in preferred forms, the second scale of indicia is derived for a length measurement of at least a portion of a body part selected from the group consisting of the humerus, ulna, tibia, and femur. Preferably, the length measurement is the half-length of the humerus and the circumference measurement is taken at the midpoint of the humerus. When the half-length of the humerus and the circumference of the midpoint of the humerus (or the MUAC as used below) are used as the measurements of the method, the first scale of indicia includes gradations 1 cm in length that are 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively. Further, in this embodiment, the second scale of indicia includes gradations 0.5 cm in length that are 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively.

DESCRIPTION OF THE FIGURES

FIG. 2: is a chart comparing other methods of estimating weight with one embodiment of the method and device of the present invention;

FIG. 4D illustrates the invention as it obtains a length measurement from the midpoint of the humerus;

FIG. 5: is an illustration of the embodiment of FIG. 3 with additional detail regarding the engagement of the two strips of the device of the present invention;

FIG. 8 is a chart comparing the mean error (ME), mean percentage error (MPE), root mean square error (RMSE), and percent agreement between estimated weight and actual weight between the method of the present invention and several conventional methods.

DETAILED DESCRIPTION

Figure 1:
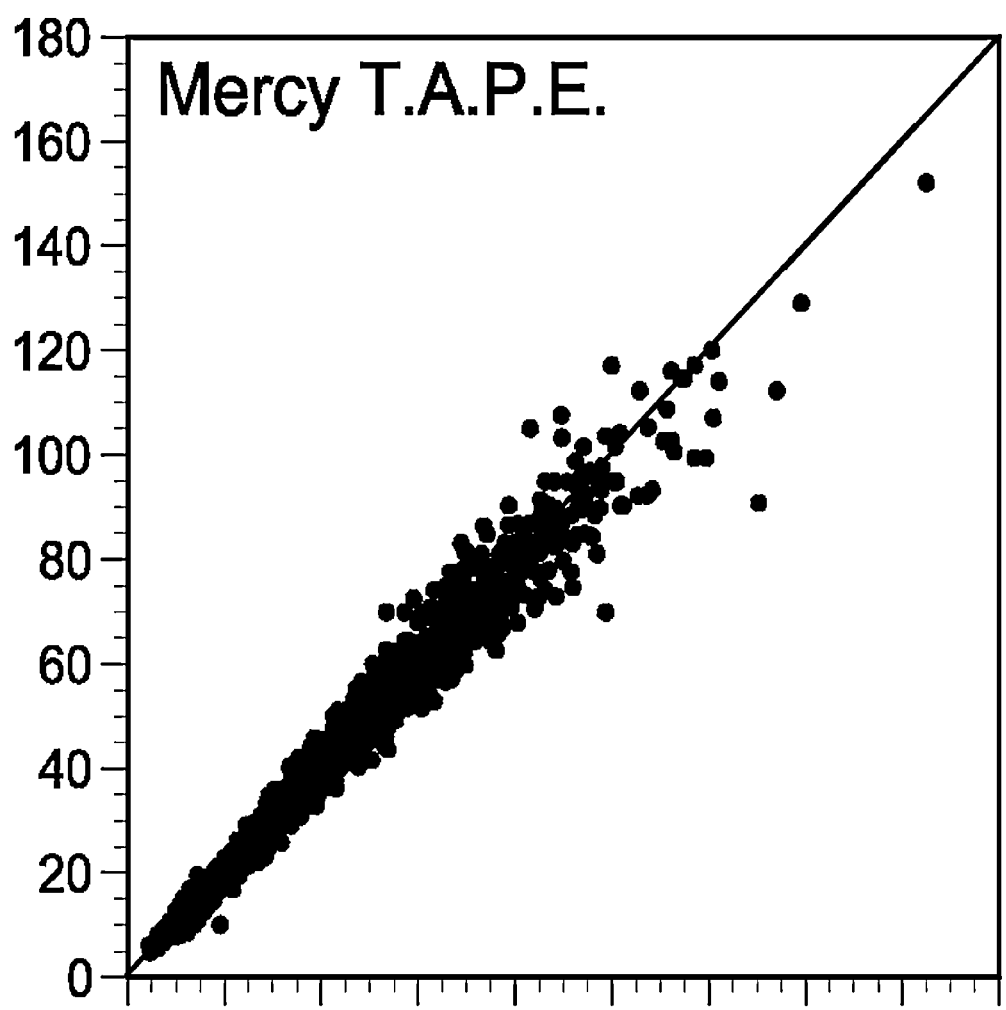
FIG. 1: is a graph illustrating data from the verification data for the device of the present invention.

In one preferred embodiment of the present invention, illustrated in FIGS. 3, 4A, 4B, 4C, 4D, 5, and 7, the device 1 comprises two strips. It is preferred that the two strips are oriented perpendicular to one another such that there is a horizontally oriented strip 10 and a vertically oriented strip 20. The horizontally oriented strip 10 preferably measures girth, while the vertically oriented strip 20 preferably measures length. The horizontal strip is preferably oriented such that it forms a circle. Preferably, one end of the horizontal strip is slidably engaged with the other end of the strip to form a loop. A fastener 12 is preferably attached to the horizontal strip 10 with a reading window 13 for the measured value. The vertical strip 20 is preferably oriented perpendicularly below the horizontal strip 10 and affixed to the horizontal strip 10 to create a single unit device 1. The horizontal strip 10 has a scale 11 printed on one side and the vertical strip 20 has a scale printed on one side 21. When the value of the scale on the horizontal strip 10 is added to the value on the vertical strip 20 a child's weight can be estimated.

Figure 6:
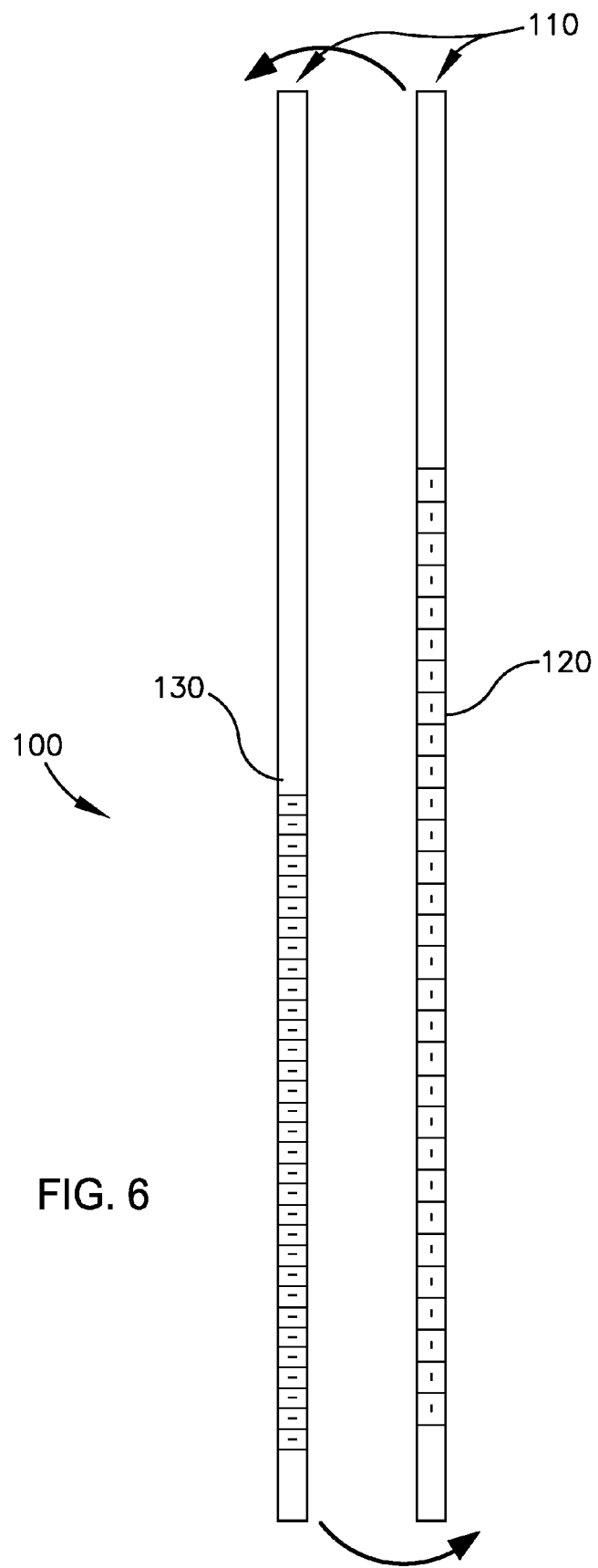
FIG. 6: is an illustration of an alternate embodiment of the device of the present invention.
Figure 7:
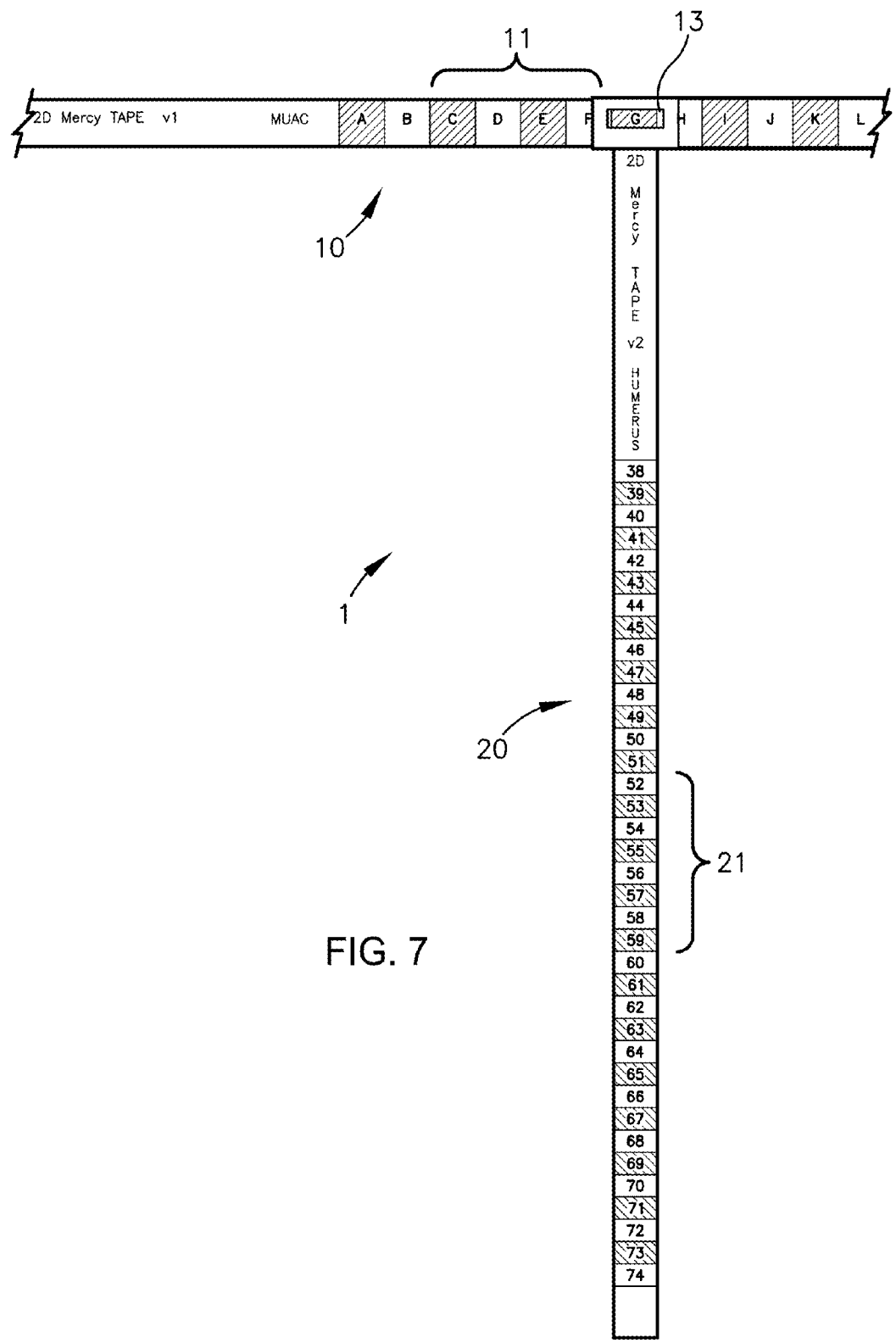
FIG. 7 is an illustration of an alternate embodiment of the device of the present invention wherein letters are used for the circumference measurement.

In a second preferred embodiment of the present invention, illustrated in FIG. 6, the device 100 comprises a single elongate flexible strip 110 having a first side 120 and an opposing second side 130, each of which include indicia printed thereon. The indicia are a scale having gradations related to a measurement. First side 120 is generally used to measure the girth or circumference of a body part. Second side 130 is generally used to measure the length of a body part. The indicia of the first side and the indicia of the second side are preferably different and specifically related to a body part. For example, the scale on first side 120 might be designed with gradations 1 cm apart that are representative of a first value when used to measure the circumference of the middle upper arm of a child between the ages of 2 months and 16 years. Similarly, the scale on the second side 130 might also be designed with gradations 1 cm apart that are representative of a second value when used to measure the length of the humerus in the same child. In preferred forms, when first and second values are determined, they are combined or added together to provide the estimated weight of the child.

FIG. 5 illustrates an embodiment of the present invention and provides direction of where to fold and where to cut the strips in order to produce an embodiment of the present invention in accordance with FIGS. 3, 4A-4D, and 7. In this Figure, the small dashed lines indicate fold lines and the larger dashed lines indicate cut lines. Additionally, the center lines are shown by way of the intersecting, cross-hair-type lines, as shown in the magnified portion of the corner of the strip.

DEFINITIONS

A "child" or "children" for purposes of the present invention include any person from birth to 18 years of age. The present invention includes a preferred embodiment where the device of the present invention is suitable for children from 2 months to 16 years of age.

A "long bone" for purposes of the present invention is a bone characterized by a shaft, the diaphysis, which is much greater in length than width. The long bones are composed mostly of compact bone and lesser amounts of marrow, which is located in the medullary cavity, and spongy bones. Most bones of the limbs, including the fingers and toes, are long bones. The long bones are preferably selected from the femurs, tibias, and fibulas of the legs, the humeri, radii, and ulnas of the arms, metacarpals and metatarsals of the hands and feet, and the phalanges of the fingers and toes. Femurs, tibias, and humeri are especially preferred.

A "measurement" for purposes of the present invention refers to the use of a device to determine a value. The value can be length, circumference, girth, etc.

"Indicia" for purposes of the present invention refers to letters, numbers, symbols, colors, and patterns.

A "strip", for purposes of the present invention, refers to a rectangular shaped segment of material that is longer than it is wide. A strip in the context of the present invention is part of the device of the present invention.

A "scale" for purposes of the present invention refers to a set of values, numbers, or indicia that represent values used to obtain the estimated weight or dose. Alternately, a scale can be a physical weight measuring machine, depending on the context in which the word "scale" is used.

"Mercy TAPE" for purposes of the present invention refers to one embodiment of the device of the present invention.

EXAMPLES

The following examples are provided for illustrative purposes only. Nothing contained herein shall be construed as a limitation of the scope of the present invention.

Example 1

This example describes the development and validation of a length- and habitus-based weight estimation method. The results were then compared with a number of other currently available weight estimation strategies and methods.

Materials and Methods

The National Health and Nutrition Examination Survey (NHANES) datasets corresponding to the years 1999-2000, 2001-2002, 2003-2004, 2005-2006 and 2007-2008 were downloaded from the CDC web site. The subset of data constituting all children aged 0 to 16 years were extracted into a separate database. Demographic and anthropometric variables of interest included age, gender, height, length, weight, middle-upper arm circumference (MUAC), and humeral length (HL). Incomplete datasets and those missing the relevant variables were excluded. A random number generator was used to partition the datasets into the "method development" and the "method validation" sets with approximately 90% and 10% of the datasets comprising the former and later groups, respectively.

The relationship between total body length and HL was explored prior to method development to confirm the utility of long bone length serving as a surrogate for total body length. Similarly, the relationships between HL or MUAC (defined as continuous variables) and weight were examined to confirm their utility as variables in an equation describing weight. Length and habitus measurements were collapsed into 1.0 cm bins creating a finite number of discrete variables by rounding MUAC and HL up or down to their nearest 1.0 cm increment. The median population weight from the method development dataset was calculated for each MUAC-HL bin pair. A statistical weighting value was assigned to each bin pair depending on the absolute number of individuals in the population that comprised the median weight of that bin pair. Additionally, an inverse weighting value was assigned to each bin pair based on the median age of the individuals that comprised the corresponding MAUC-HL bin. Two-dimensional least-squares regression was undertaken to identify a fractional weight assignment that would minimize the goodness-of-fit criteria for each HL bin across all MUAC bins, for each MUAC bin across all HL bins, and for all MUAC and HL bins taken together. A weight estimate was generated for each individual by the simple addition of the MUAC and HL fractional bin values that correspond to that individual's measurements.

The remaining 10% of data were used as an internal validation set. The MUAC and HL of each child was rounded up or down to the nearest 1.0 cm bin (e.g. HL of 19.2 is rounded down to 19, MUAC of 32.7 rounded up to 33). The corresponding fractional weight for each variable was identified and summed to generate a weight estimate for that child. The age and/or length of each child was also used to generate a predicted weight using other previously published weight estimation strategies (FIG. 2). For each estimation method, no weight was estimated if the child's age and/or height fell outside of the bounds established for that method (e.g. weight would not be estimated using; the Broselow method for a 158 cm child, the Theron method for a 6 month old infant, etc).

Initial model development was performed with MUAC and HL; however, model development was then refined using half-humeral length (HHL) for development of the tool. This change was made because MUAC is determined at the midpoint of the humerus and the incorporation of a half-humeral measurement into the model would permit the construction of a simple tool that can simultaneously measure both variables at once. Validation was repeated using MUAC and HHL rounded to the nearest 1.0 and 0.5 cm, respectively to confirm that the model returned identical performance statistics to the MUAC-HL model. Once confirmed, a 2-dimensional image was constructed consisting of adjacent perpendicular measuring strips partitioned to correspond to the respective MUAC and HHL bins. The image was cut out and the product folded in a specific manner to generate a 3-dimensional measuring device which permits the assessment of MUAC and HHL at one time. The device does not register a centimeter length reading for MUAC and HHL but rather directly displays the fractional weight corresponding to each variable such that the two values are simply added together with no additional conversion or external reference required. Alternatively, the tool can be constructed as a singular strip with bins for MUAC mapped on one side and bins for HHL mapped on the other. This version would require two independent measurement steps followed by addition as is done with the 3D unit. For populations with less variability in height or weight, the number of MUAC and HHL bins can be truncated with no introduction of error.

The predicted weight of each child was plotted against their actual weight to evaluate the predictive performance of the mathematical model developed in this study (the "Mercy" method). Linear regression was used to evaluate the relationship between the actual and predicted weights by calculating the slope, the 95% confidence interval (CI) for the slope, the intercept and the correlation coefficient. Mean error (ME) was calculated by taking the difference of the predicted and actual weights. Mean percentage error (MPE) between predicted and actual weight was calculated by dividing by the actual weight into the ME and multiplying by 100. Fortuitous cancellation of errors with different signs was examined by computing the root mean square error (RMSE) calculated by taking the square root of the average squared error. The percent agreement between estimated weight and actual weight was also reported (See, FIG. 8). The validation data were also applied to the previously published weight estimation methods and their predictive performances were compared with the method of the present invention. All mathematical and statistical analyses were performed with Microsoft Excel 2003 and SPSS v 12.0.

Results and Discussion

Only children greater than 2 months of age in the NHANES database had humeral length and MUAC recorded. When children under the age of 2 months were removed, along with the remaining incomplete data sets, a total of 19,266 pediatric datasets were available. Of these, 17,328 constituted the method development set and the remaining 1,938 comprised the method validation set. The regression parameter estimates for our method compared with other weight-estimation strategies are provided below in FIG. 2. As shown in FIG. 1, the method of the present invention comes closest to achieving the desired characteristics of fit (i.e. slope approaching one, intercept approaching zero, correlation coefficient approaching one) when compared with the other published methods. Using the present methods, a weight could be predicted for all 1,938 children in the validation set as compared with 27-90% of children using the other weight estimation strategies (FIG. 2).

When examined for bias and precision, the methods of the present invention proved to be superior to all other weight estimation strategies that were evaluated (see FIG. 8). The methods of the present invention demonstrated a significantly lower MPE, ME and RMSE than any of the other methods ($p<0.01$). Further, only the present method estimated weights within 10% of actual for the majority of children in the validation set (79% vs. 16 to 45%). The performance criteria observed for the previously published methods were consistent with those reported for these same methods in other validation and comparison driven investigations.

Given that previously published methods tend to perform poorly at the extremes of weight, the validation datasets were segregated by body-mass index (BMI) percentile and the present method was compared with the other weight estimation strategies by subgroup (note: infants under the age of 2 years are not routinely stratified into weight classes). As depicted in FIG. 8, the Mercy method performs robustly with minimal bias across the spectrum of ages and weight classes observed in this study.

Weight estimation techniques address a critical medical need in both developing and developed countries. They permit the determination of accurate weight-based doses in situations where there is neither the time nor the opportunity to directly weigh patients on a calibrated scale. Numerous weight estimation strategies have been described with each used to varying degrees in clinical practice. Though many have distinct advantages (e.g. simple age-based equations can be used without the need for reference materials, preprinted tables/tools limit the risk of calculation errors) most have significant limitations. Relatively few methods have been evaluated in multiple different pediatric populations and essentially no single previous method provides accurate estimates of weight across broad age- and weight-bands.

Most of the age- and length-based strategies examined in this example overestimated weight in children classified, by BMI, as underweight and underestimated weight in children classified as overweight or obese. The degree to which this occurred depended largely on the constants driving their mathematical equations, with some methods biased toward more accurate prediction in children of lower weight (e.g. Broselow) and others performing better among children in the higher weight brackets (e.g. Theron). Irrespective of directionality, the bias observed with some methods in children at the extremes of weight represented as much as a 3-fold error between predicted and actual weights. Discrepancies of this magnitude can be dangerous, and potentially life-threatening, depending on how 'forgiving' the intervention or treatment that is being administered.

The singular habitus-based method (i.e. Cattermole) ranked among the best with respect to absolute bias and precision irrespective of BMI percentile. This is consistent with the finding that the relationship between weight and MUAC tends to be linear within any given population. Accordingly, MUAC-based methods should perform well in relatively homogenous populations although a greater degree of variance should be expected when compared with a method that incorporates both stature and girth. Given the nature of the data used to develop and validate the Mercy method, the performance of the method of the present invention could not be compared to the Devised Weight Estimation Method (DWEM), which was the only other method to incorporate both body length and body habitus. Notably, the latter estimate involves a subjective rating of "slim," "average," or "heavy". While DWEM has been demonstrated to outperform age-based methods, the categorical assignment of habitus coupled with inconsistencies in subjective assessment between and within observers [inter-rater agreement—78% (range: 58-93%); intra-rater agreement—86% (range: 81-94%)] contributed to bias and precision estimates that were larger than observed with strategies based on length.

The method developed herein attempts to address several limitations inherent in the existing weight estimation strategies. As with other strategies, the method of the present invention incorporates growth velocity but uses humeral length as a surrogate for total body length. Restricting length measurements to a single long bone minimizes the discrepancies that result from whether the measurement is obtained with the child standing or lying down and may be easier and faster to obtain that total body length in a child who is uncooperative or obtunded. The method of the present invention also incorporates habitus as a continuous variable which improves the accuracy of the overall length-based weight estimate and removes the subjective nature of categorizing the child's body type into one of a few alternatives. By developing a model with these considerations in mind, the present invention was able to expand the age range to which the weight estimation method can be applied and removed length restrictions which are typically imposed because of the disproportionate increase in weight-for-height observed as children get older. The combination of HL and MUAC as the length and habitus surrogates of choice for this investigation arise from the natural relationship between these two measurements, namely that MUAC is determined at the midpoint of the humerus and access to a single long bone can quickly yield both measurements.

Limitations nested within this example include the fact that the NHANES data were collected by numerous raters not including the authors. As such, there is no mechanism to assess inter-rater reliability with respect to the precision of MUAC and HL measurements. In addition, the data span a collection range of 10 years which could fail to account for changing height-for-weight patterns over time. Nonetheless, the method of the present invention (the "Mercy Method") performed robustly irrespective of these limitations. Subsequent prospective evaluation of the Mercy Method necessitates a study design that incorporates assessment of both inter-rater and intra-rater reliability to explore the full utility of the method described herein.

The Mercy Method was designed for use as a reference table or a measuring device (i.e. the Mercy TAPE™) that performs assessments of length and girth simultaneously. The device can be printed on any flexible, non-stretchable medium (e.g. paper, plastic coated paper, fiberglass) so as to be disposable or semi-permanent. In its numeric form, the Mercy TAPE would have limited utility in settings where care providers are illiterate or do not use a written language. However, the tool could be easily revised with colors and/or symbols whose combination would correspond to a given dose, intervention strategy or weight target.

Example 2

This example illustrates a method of using the device of the present invention to estimate weight.
Materials and Methods An embodiment of the device of the present invention was used incorporating two strips oriented perpendicular to each other having a horizontal strip 10 and a vertical strip 20. The scale used for measuring girth was as follows:

2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively.

Each value (in kilograms) represented a 1 cm length or space on the strip.

The girth value measured from the patient was 20.1

The scale used for measuring length was as follows:

0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively.

Each value (in kilograms) represented a ½ cm space on the strip.

The length value measured for the patient was 23. Thus, the total of both measurements was 43.1 kilograms or 94.8 lbs. When the patient was weighed using a conventional scale, the weight was determined to be 95 lbs.

Figure 3:
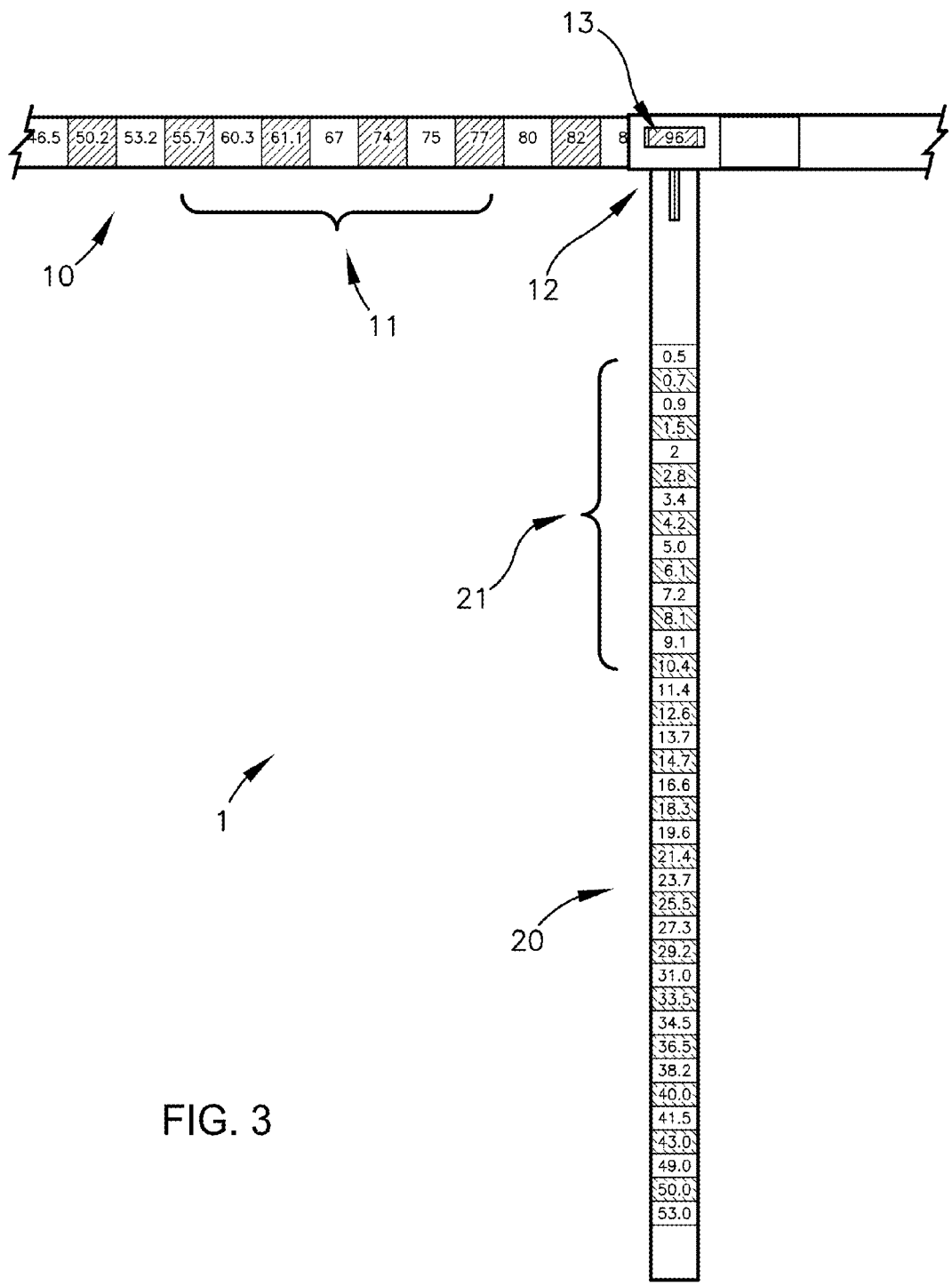
FIG. 3: is an illustration of a partial view of one embodiment of the device of the present invention (Mercy TAPE)
Figure 4A:
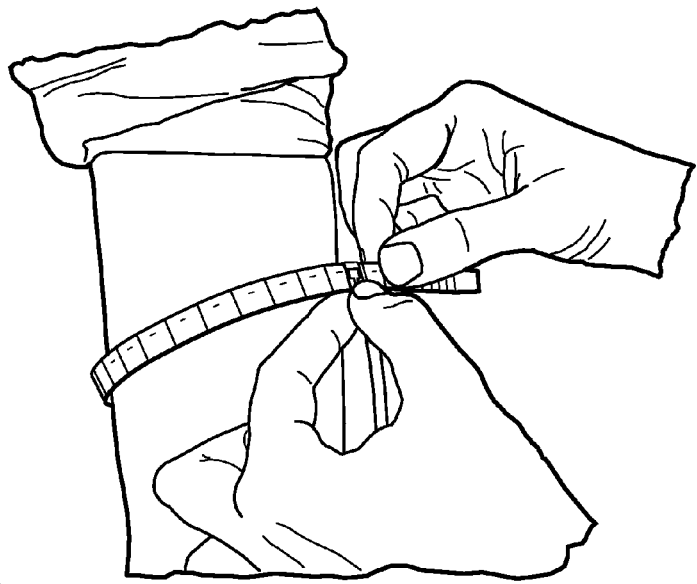
FIG. 4A illustrates application of one embodiment of the invention to the middle of the upper arm.
Figure 4B:
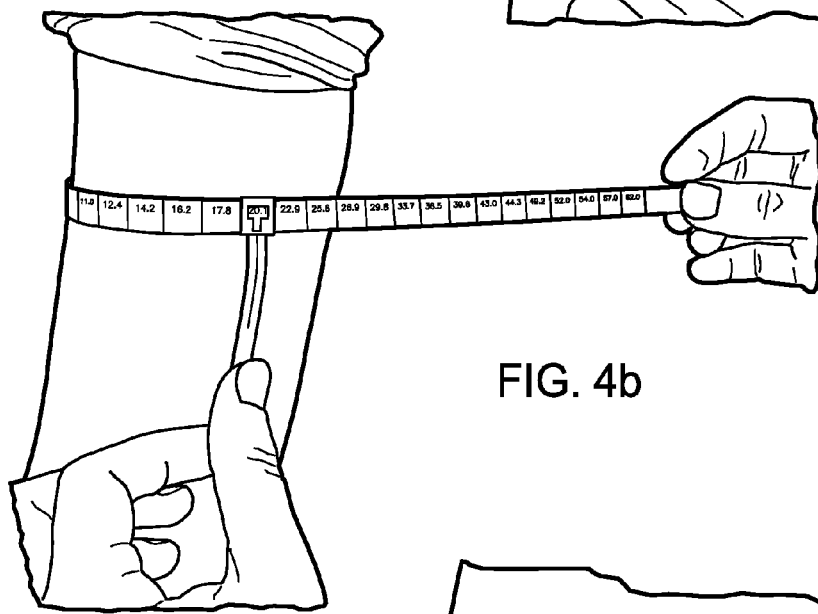
FIG. 4B illustrates one embodiment of the invention as the device of the invention is pulled tight to measure the circumference of the middle of the upper arm.
Figure 4C:
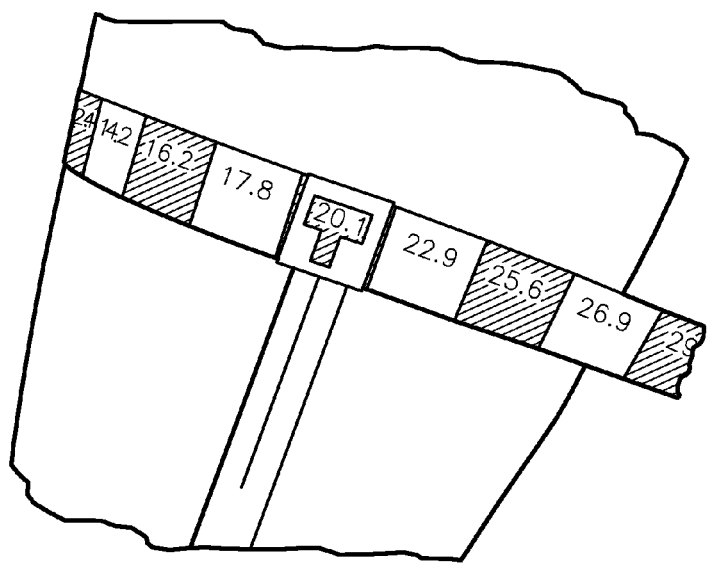
FIG. 4C illustrates one embodiment of the invention showing the value received when measuring the circumference of a body part.

One end of the horizontal strip 10 was slidably engaged with the other end of the horizontal strip such that it fit around the upper arm of a child. The vertical strip 20 was attached to the horizontal strip in a perpendicular orientation. The circular horizontal strip 10 was placed around the child's upper arm in the center of the upper arm. The value corresponding with the girth of the arm was recorded. The vertical strip 20 was used to measure half of the length of the humerus of the child and the value was recorded. The girth value was added to the length value to determine the weight of the child in kilograms. The weight of the child was used to determine the appropriate dose of medication for the child. The weight of the child was then taken using a scale to determine the actual weight of the child. FIG. 3 provides a partial view of the actual device used for this embodiment of the present invention. FIG. 4 illustrates how the device was used in this example.

Results and Discussion

The child's weight was accurately determined as 94.8 lbs or 43.1 kilograms. As this estimating tool has been validated, an appropriate dose of medication could be administered to the child based on the outcome of this Example.

Example 3

This example illustrates a method of using the device of the present invention to estimate weight.
Materials and Methods An embodiment of the device of the present invention incorporating one strip that will be printed on both sides was used, wherein one side had a scale for girth and the other side had a scale for length.

The side of the strip printed with a scale for girth was used to measure the girth of either the upper leg, upper arm, or neck. This value was recorded. The side of the strip printed with a scale for length was used to measure the length or half of the length of a long bone in the body selected from the humerus, tibia, or ulna. The value was recorded. The girth value was then added to the length value to estimate the weight of the child in kilograms. The weight of the child was used to determine the appropriate dose of medication for the child. The weight of the child was then taken using a scale to determine the actual weight of the child and the estimated weight was compared to the actual (or measured weight).

Results and Discussion

The child's weight was accurately determined and the dose administered to the child was therefore appropriate.

Example 4

This example illustrates an embodiment of the method of the present invention utilizing indicia or symbols.

Materials and Method

A device of the present invention incorporating one scale for girth and one scale for length will be used to obtain measurements from a child. The scale for girth will consist of a set of symbols. The symbols can be any symbols, such as a heart, star, square, circle, triangle, etc. The scale for length will consist of letters, such as A, B, C, D, E, etc (See FIG. 7 for an example). The device printed with the scales for girth and length will be either a two strip or a one strip embodiment of the device. The strip printed with the scale for girth will be used to measure the girth of the upper arm, upper leg, or neck. The symbol corresponding with the girth measurement will be recorded. The strip printed with the scale for length will be used to measure the length or half of the length of a long bone, such as the humerus, tibia, or ulna. The letter corresponding to the length or half of the length long bone will be recorded. The resulting symbol/letter combination, such as A/star, B/heart, C/square, etc. will be used to determine the appropriate dose of medication by using a reference chart that pairs a symbol/letter combination with a dose of medication.

Results and Conclusions

The dose determined from the reference chart using the symbol/letter combination will be appropriate for the weight of the child. It can be seen that this embodiment requires additional conversions that are not necessary when the gradations relate to the actual weight values that are to be added together to estimate weight (as in the earlier embodiments).

Example 5

This example illustrates that the method of the present invention is useful and accurate in estimating the weight of children from 2 months to 16 years of age and of varying geographic and ethnic origin than in Example 1.

Materials and Methods

In total, 473 children were enrolled in this study. The demographic and anthropometric constitution of the children enrolled from Ouelessebougou, Mali are detailed below in Table 1.

TABLE 1

T.A.P.E.-Mali Demographic and Anthropometric Summary Statistics

| Parameter | Mean ± SD |
|---|---|
| enrollment | 473 |
| male (%) | 47 |
| female (%) | 53 |
| age (yr) | 8.1 ± 4.8 |
| weight (kg) | 25.1 ± 14.5 |
| height (cm) | 120.9 ± 29.5 |
| Armspan (cm) | 125.1 ± 32.3 |
| Humerus (cm) | 25.3 ± 6.8 |
| MUAC (cm) | 17.8 ± 3.7 |
| ulna (cm) | 20.1 ± 5.5 |
| tibia (cm) | 26.0 ± 8.2 |
| BMI (kg/m2) | 15.6 ± 2.4 |
| BMI percentile | 23.1 ± 23.5 |
| infant (%) | 11.7 |
| underweight (%) | 21.8 |
| normal (%) | 64.8 |
| overweight (%) | 1.3 |
| Obese (%) | 0.4 |

There were slightly more female (n=252) than male (221) participants enrolled in the study. Participating children were evenly distributed across the spectrum of age from 2 months to 16 years with an average age of 8.1±4.8 years. Expectedly, the population distribution for height was positively skewed and the distribution for weight negatively skewed resulting in an average BMI (15.6±2.4 kg/m2) and BMI percentile (23.1±23.5) that favored children who were underweight or normal (as classified by the Centers for Disease Control).

The Mercy method was applied to the data to evaluate its predictive performance. The mid-upper arm circumference (MUAC) and humeral length (HL) measures for each child were rounded up or down to the nearest 1.0 cm bin and the corresponding fractional weight for each bin assigned. The fractional weights for MUAC and HL were then summed to generate an estimated weight for that child. The age and/or length reported for each child was also used to generate a predicted weight using other previously published weight estimation strategies.

The predicted weight of each child was plotted against their actual weight to evaluate the predictive performance of the Mercy method. Linear regression was used to evaluate the relationship between the actual and predicted weights by calculating the slope, the 95% confidence interval (CI) for the slope, the intercept and the correlation coefficient. Mean error (ME) was calculated by taking the difference of the predicted and actual weights. Mean percentage error (MPE) was calculated by dividing by the actual weight into the ME and multiplying by 100. Root mean square error (RMSE) was calculated by taking the square root of the average squared error. The percent agreement between estimated weight and actual weight was also examined. All analyses were performed with Microsoft Excel 2003 and SPSS v11.5.

Results and Discussion

The Mercy method performed extremely well when applied to children enrolled in Mali. The method predicted a weight in all but three children (99.4%) whose humeral length exceeded the upper bound for the method. However, when the largest fractional weight for humeral length was assigned to these three children, the predicted weight was within 4.1, 4.5, and 11.5% of actual weight for each child, respectively. Thus, all children were considered to have a weight predicted by the Mercy method. Prediction rates for thirteen other published weight estimation methods ranged from 36-94%. The regression parameters generated by the comparison of actual and predicted weights are detailed in Table 2.

TABLE 2

Regression parameters generated from the plot of actual vs. predicted weight for children enrolled from Mali

| method | n | slope | 95% CI | intercept | 95% CI | $r^2$ |
|---|---|---|---|---|---|---|
| Mercy | 473 | 0.957 | 0.941, 0.972 | 1.134 | 0.679, 1.590 | 0.968 |
| APLS | 296 | 0.792 | 0.746, 0.838 | 4.649 | 3.774, 5.525 | 0.796 |
| ARC | 446 | 0.863 | 0.829, 0.896 | 5.163 | 4.161, 6.166 | 0.852 |
| Argall | 296 | 1.308 | 1.232, 1.384 | 1.072 | −0.373, 2.516 | 0.796 |
| Best Guess | 429 | 1.194 | 1.146, 1.242 | 2.889 | 1.684, 4.095 | 0.847 |
| Broselow | 365 | 1.047 | 1.021, 1.073 | 0.617 | 0.091, 1.144 | 0.945 |
| Cattermole | 170 | 0.799 | 0.719, 0.879 | 3.041 | 1.101, 4.890 | 0.700 |
| Leffler | 323 | 0.889 | 0.843, 0.934 | 4.572 | 3.744, 5.400 | 0.824 |
| Luscombe & Owens | 296 | 1.189 | 1.120, 1.258 | 1.974 | 0.661, 3.287 | 0.796 |
| Nelson | 369 | 1.174 | 1.116, 1.234 | 0.720 | −0.527, 1.968 | 0.808 |
| Shann | 446 | 0.720 | 0.693, 0.748 | 7.983 | 7.167, 8.799 | 0.858 |
| Theron | 296 | 1.758 | 1.645, 1.872 | −5.278 | −7.432, −3.123 | 0.760 |
| Traub-Johnson | 446 | 0.999 | 0.974, 1.024 | 2.105 | 1.368, 2.842 | 0.935 |
| Traub-Kichen | 446 | 0.901 | 0.879, 0.924 | 3.745 | 3.073, 4.418 | 0.933 |

As shown above, the Mercy method offers the best correlation (r2=0.968) when compared to other methods (range: 0.760-0.945) and comes among the closest to achieving the desired characteristics of fit (i.e. slope approaching one, intercept approaching zero). When examined for bias and precision, the Mercy method outperformed the other weight estimation strategies demonstrating a lower ME, MPE and RMSE (Table 3).

TABLE 3

Predictive performance of the Mercy method and other weight estimation methods on data from children enrolled in Mali

| | | ME | | MPE | | |
|---|---|---|---|---|---|---|
| method | n | mean | stdev | mean | stdev | RMSE |
| Mercy | 473 | 0.06 | 2.58 | 1.6 | 9.3 | 2.58 |
| APLS | 296 | 0.92 | 2.84 | 7.8 | 14.7 | 2.98 |
| ARC | 446 | 1.61 | 5.48 | 9.6 | 18.0 | 5.71 |
| Argall | 296 | 6.60 | 4.58 | 36.0 | 21.9 | 8.03 |
| Best Guess | 429 | 7.20 | 6.28 | 32.7 | 22.6 | 9.55 |
| Broselow | 365 | 1.50 | 2.00 | 8.2 | 10.4 | 2.49 |
| Cattermole | 170 | −1.75 | 2.77 | −6.8 | 11.5 | 10.7 |
| Leffler | 323 | 2.67 | 2.87 | 18.7 | 18.6 | 3.91 |
| Luscombe & Owens | 296 | 5.37 | 3.96 | 30.0 | 19.6 | 6.67 |
| Nelson | 369 | 4.10 | 5.30 | 19.8 | 21.6 | 6.70 |
| Shann | 446 | 0.73 | 5.72 | 9.7 | 18.6 | 5.76 |
| Theron | 296 | 8.37 | 7.83 | 42.1 | 31.7 | 11.45 |
| Traub-Johnson | 446 | 2.15 | 3.66 | 9.0 | 11.5 | 4.24 |
| Traub-Kichen | 446 | 1.24 | 3.66 | 7.4 | 11.5 | 3.76 |

The Mercy method estimated weights within 10% of actual for the majority of children in the study (71%) as opposed to the other methods for which weight was predicted to within 10% of actual for a minority of the participating children (range 8-47%) (Table 4). As most of the published methods tend to perform poorly at the extremes of weight, the data from Mali were segregated by BMI percentile and the Mercy method examined independently for infants and children who were underweight, normal, overweight and obese. Advantageously, the Mercy method performed with comparable predictive power irrespective of BMI classification.

TABLE 4

Cumulative percentage agreement between predicted weight and actual weight in the data from Mali

| | | percentage in agreement within: | | | | | | | | | | |
|---|---|---|---|---|---|---|---|---|---|---|---|---|
| method | n | 10% | 20% | 30% | 40% | 50% | 60% | 70% | 80% | 90% | 100% | >100% |
| Mercy | 473 | 71.5 | 96.7 | 99.9 | 100 | 100 | 100 | 100 | 100 | 100 | 100 | 100 |
| APLS | 296 | 30.2 | 49.9 | 57.9 | 61.3 | 62.6 | 62.6 | 62.6 | 62.6 | 62.6 | 62.6 | 62.6 |
| ARC | 446 | 40.8 | 68.7 | 82.2 | 88.3 | 92.8 | 93.1 | 93.7 | 93.9 | 94.1 | 94.1 | 94.1 |
| Argall | 296 | 8.2 | 15.6 | 22.2 | 34.0 | 46.9 | 54.5 | 58.5 | 61.3 | 61.8 | 62.2 | 62.4 |
| Best Guess | 429 | 11.2 | 26.6 | 40.8 | 59.0 | 73.6 | 81.0 | 85.0 | 88.8 | 89.3 | 90.0 | 90.4 |
| Broselow | 365 | 41.2 | 67.4 | 75.1 | 77.0 | 77.2 | 77.2 | 77.2 | 77.2 | 77.2 | 77.2 | 77.2 |
| Cattermole | 170 | 19.7 | 31.3 | 35.3 | 35.9 | 35.9 | 35.9 | 35.9 | 35.9 | 35.9 | 35.9 | 35.9 |
| Leffler | 323 | 17.3 | 37.8 | 49.6 | 59.3 | 64.8 | 67.5 | 67.7 | 68.1 | 68.1 | 68.1 | 68.1 |
| Luscombe & Owens | 296 | 10.1 | 18.3 | 30.8 | 43.3 | 53.4 | 58.5 | 61.5 | 61.9 | 62.5 | 62.5 | 62.5 |
| Nelson | 369 | 23.5 | 40.4 | 54.6 | 65.6 | 71.5 | 74.2 | 76.7 | 76.9 | 78.0 | 78.0 | 78.0 |
| Shann | 446 | 35.1 | 62.6 | 78.7 | 89.3 | 92.9 | 94.0 | 94.2 | 94.4 | 94.4 | 94.4 | 94.4 |

TABLE 4-continued

Cumulative percentage agreement between predicted weight and actual weight in the data from Mali

| method | n | \multicolumn{11}{c}{percentage in agreement within:} |
|---|---|---|---|---|---|---|---|---|---|---|---|---|

| method | n | 10% | 20% | 30% | 40% | 50% | 60% | 70% | 80% | 90% | 100% | >100% |
|---|---|---|---|---|---|---|---|---|---|---|---|---|
| Theron | 296 | 8.5 | 14.6 | 25.0 | 32.2 | 40.9 | 47.9 | 52.1 | 55.7 | 57.4 | 59.5 | 62.7 |
| Traub-Johnson | 446 | 44.2 | 81.0 | 91.4 | 93.7 | 94.1 | 94.1 | 94.1 | 94.1 | 94.3 | 94.3 | 94.3 |
| Traub-Kichen | 446 | 47.4 | 83.6 | 92.5 | 93.8 | 94.2 | 94.2 | 94.2 | 94.4 | 94.4 | 94.4 | 94.4 |

Overall, the Mercy method performed exceedingly well in the T.A.P.E.-Mali study. The predictive performance of the method in Malian children appears comparable to the performance of the method in U.S. children. Although data on height, arm span and other long bones were collected in anticipation of the need to develop a Mali-specific method, it does not appear that modification of the existing Mercy method is required for accurate weight estimation in Malian children.

Weight estimation strategies address a critical medical need in settings where there is neither the time nor the opportunity to directly weigh patients. To date, no single previous method has provided accurate estimates of weight across a broad range of ages, weights and lengths. The Mercy method attempts to address limitations inherent in the existing weight estimation strategies. It expands the age range of children to which a single weight estimation method can be applied and removes length restrictions observed in other commonly used methods. T.A.P.E.-Mali is the second prospective evaluation of the Mercy method in non-U.S. children. The results of this study suggest that the utility of Mercy method extends beyond the U.S.

Example 6

This example illustrates that the method of the present invention is useful and accurate in estimating the weight of children from 2 months to 16 years of age and of varying geographic and ethnic origin than in Examples 1 and 5.

Materials and Methods

In total, 784 children were enrolled from two study sites in this study. The demographic and anthropometric constitution of the children enrolled from Cuttack and Pondicherry, India are detailed below in Table 5.

TABLE 5

| parameter | Cuttack | Pondicherry |
|---|---|---|
| enrollment | 375 | 409 |
| male (%) | 50.1 | 44.7 |
| female (%) | 49.9 | 55.3 |
| age (yr) | 7.5 ± 4.3 | 9.0 ± 4.9 |
| weight (kg) | 22.1 ± 12.3 | 26.5 ± 13.8 |
| height (cm) | 116.2 ± 26.3 | 125.5 ± 28.1 |
| armspan (cm) | 115.6 ± 27.3 | 126.1 ± 30.4 |
| humerus (cm) | 23.7 ± 5.9 | 24.0 ± 6.0 |
| humerus adjusted | N/A | 25.7 ± 6.3 |
| MUAC (cm) | 16.9 ± 3.7 | 17.9 ± 3.5 |
| ulna (cm) | 18.6 ± 4.6 | 20.1 ± 4.9 |
| tibia (cm) | 25.8 ± 7.5 | 28.4 ± 8.2 |
| BMI (kg/m$^2$) | 15.1 ± 2.9 | 15.5 ± 2.8 |
| BMI percentile | 22.9 ± 30.7 | 19.3 ± 25.6 |
| infant (%) | 12.0 | 10.3 |
| underweight (%) | 39.5 | 40.3 |
| normal (%) | 40.0 | 50.0 |

TABLE 5-continued

| parameter | Cuttack | Pondicherry |
|---|---|---|
| overweight (%) | 2.9 | 2.9 |
| obese (%) | 5.6 | 0.5 |

There were slightly more female (n=413) than male (371) participants enrolled in the study. Participating children were evenly distributed across the spectrum of age from 2 months to 16 years with an average age of 8.3±4.7 years. Expectedly, the population distribution for weight was positively skewed and the distribution for height negatively skewed resulting in an average BMI (15.3±2.8 kg/m$^2$) and BMI percentile (21.0±28.1) that favored children who were underweight or normal (as classified by the Centers for Disease Control). Children from the Cuttack site were younger and consequently smaller than the children enrolled in Pondicherry (Table 5); however, the distribution of children by BMI category did not differ substantially between sites.

The Mercy method was applied to the data to evaluate its predictive performance. The mid-upper arm circumference (MUAC) and humeral length (HL) measures for each child were rounded up or down to the nearest 1.0 cm bin and the corresponding fractional weight for each bin assigned. The fractional weights for MUAC and HL were then summed to generate an estimated weight for that child. The age and/or length reported for each child was also used to generate a predicted weight using other previously published weight estimation strategies.

The predicted weight of each child was plotted against their actual weight to evaluate the predictive performance of the Mercy method. Linear regression was used to evaluate the relationship between the actual and predicted weights by calculating the slope, the 95% confidence interval (CI) for the slope, the intercept and the correlation coefficient. Mean error (ME) was calculated by taking the difference of the predicted and actual weights. Mean percentage error (MPE) was calculated by dividing by the actual weight into the ME and multiplying by 100. Root mean square error (RMSE) was calculated by taking the square root of the average squared error. The percent agreement between estimated weight and actual weight was also examined. All analyses were performed with Microsoft Excel 2003 and SPSS v11.5.

Results and Discussion

The Mercy method performed extremely well when applied to children enrolled in India. The method predicted a weight in all but one child whose MUAC fell below the lower bound for the method. Prediction rates for thirteen other published weight estimation methods ranged from 32-95%. The regression parameters generated by the comparison of actual and predicted weights are detailed in Tables 6a and 6b.

TABLE 6a

Regression parameters generated from the plot of actual vs. predicted weight for children enrolled from Cuttack, India.

| method | n | slope | 95% CI | intercept | 95% CI | $r^2$ |
|---|---|---|---|---|---|---|
| Mercy | 374 | 0.927 | 0.910-0.945 | 1.488 | 1.045-1.932 | 0.967 |
| APLS | 249 | 0.495 | 0.436-0.553 | 10.272 | 9.114-11.430 | 0.531 |
| ARC | 350 | 0.779 | 0.718-0.840 | 7.952 | 6.365-9.540 | 0.646 |
| Argall | 249 | 0.742 | 0.654-0.829 | 9.408 | 7.671-11.144 | 0.531 |
| Best Guess | 347 | 0.967 | 0.895-1.039 | 7.990 | 6.287-9.693 | 0.669 |
| Broselow | 321 | 0.636 | 0.569-0.703 | 7.436 | 5.996-8.877 | 0.517 |
| Cattermole | 151 | 1.105 | 1.026-1.185 | −4.534 | −6.558-2.509 | 0.835 |
| Leffler | 247 | 0.594 | 0.530-0.658 | 9.431 | 8.297-10.564 | 0.576 |
| Luscombe-Owens | 249 | 0.742 | 0.654-0.829 | 10.408 | 8.671-12.144 | 0.531 |
| Nelson | 329 | 0.887 | 0.815-0.959 | 6.872 | 5.241-8.503 | 0.643 |
| Shann | 350 | 0.644 | 0.594-0.693 | 10.408 | 9.112-11.704 | 0.652 |
| Theron | 249 | 1.136 | 0.998-1.273 | 6.514 | 3.787-9.242 | 0.518 |
| Traub-Johnson | 350 | 0.869 | 0.830-0.908 | 4.777 | 3.750-5.804 | 0.844 |
| Traub-Kichen | 344 | 0.787 | 0.750-0.823 | 6.186 | 5.223-7.148 | 0.840 |

TABLE 6b

Regression parameters generated from the plot of actual vs. predicted weight for children enrolled from Pondicherry, India.

| method | n | slope | 95% CI | intercept | 95% CI | $r^2$ |
|---|---|---|---|---|---|---|
| Mercy | 409 | 0.893 | 0.876-0.910 | 1.897 | 1.381-2.412 | 0.962 |
| APLS | 212 | 0.67 | 0.610-0.729 | 6.988 | 5.839-8.137 | 0.699 |
| ARC | 388 | 0.928 | 0.884-0.971 | 5.069 | 3.747-6.392 | 0.822 |
| Argall | 212 | 1.004 | 0.915-1.094 | 4.482 | 2.759-6.206 | 0.699 |
| Best Guess | 329 | 1.167 | 1.105-1.230 | 4.142 | 2.600-5.684 | 0.807 |
| Broselow | 282 | 0.927 | 0.889-0.965 | 3.130 | 2.316-3.944 | 0.890 |
| Cattermole | 130 | 0.986 | 0.912-1.060 | −2.309 | −4.185--0.432 | 0.845 |
| Leffler | 212 | 0.861 | 0.794-0.929 | 5.265 | 4.137-6.393 | 0.752 |
| Luscombe-Owens | 212 | 1.004 | 0.915-1.094 | 5.482 | 3.759-7.206 | 0.699 |
| Nelson | 294 | 1.124 | 1.057-1.192 | 2.449 | 0.916-3.982 | 0.785 |
| Shann | 388 | 0.77 | 0.735-0.806 | 7.909 | 6.812-9.006 | 0.823 |
| Theron | 212 | 1.551 | 1.418-1.684 | −1.040 | −3.598-1.518 | 0.715 |
| Traub-Johnson | 388 | 0.94 | 0.902-0.978 | 4.251 | 3.095-5.407 | 0.861 |
| Traub-Kichen | 1385 | 0.849 | 0.815-0.884 | 5.712 | 4.652-6.772 | 0.860 |

As shown above, the Mercy method offers the best correlation (r2=0.962, 0.967) when compared to other methods (range: 0.517-0.890) and comes among the closest to achieving the desired characteristics of fit (i.e. slope approaching one, intercept approaching zero). When examined for bias and precision, the Mercy method outperformed the other weight estimation strategies demonstrating a lower ME, MPE and RMSE (Tables 7a and 7b).

TABLE 7a

Predictive performance of the Mercy method and other weight estimation methods on data collected from children enrolled in Cuttack, India.

| | | ME | | MPE | | RMSE | |
|---|---|---|---|---|---|---|---|
| | n | Mean | Std. Dev. | Mean | Std. Dev. | Mean | Std. Dev. |
| Mercy | 374 | −0.12 | 2.29 | 1.51 | 9.94 | 1.64 | 1.60 |
| APLS | 249 | 1.13 | 5.63 | 13.94 | 24.80 | 4.12 | 4.00 |
| ARC | 350 | 2.82 | 7.36 | 18.11 | 27.27 | 5.82 | 5.31 |
| Argall | 249 | 4.74 | 6.10 | 31.48 | 30.95 | 6.29 | 4.47 |
| Best Guess | 347 | 7.30 | 7.78 | 41.33 | 33.17 | 8.55 | 6.37 |
| Broselow | 321 | 1.22 | 3.83 | 10.76 | 16.28 | 2.95 | 2.73 |
| Cattermole | 151 | −1.92 | 4.23 | −9.76 | 18.14 | 3.66 | 2.86 |
| Leffler | 247 | 3.00 | 5.06 | 27.84 | 28.47 | 4.70 | 3.53 |
| Luscombe-Owens | 249 | 5.74 | 6.10 | 38.05 | 31.50 | 7.02 | 4.56 |
| Nelson | 329 | 4.63 | 7.36 | 28.24 | 31.61 | 6.52 | 5.75 |
| Shann | 350 | 2.13 | 7.04 | 18.36 | 27.11 | 5.56 | 4.81 |
| Theron | 249 | 8.97 | 9.05 | 51.45 | 42.64 | 9.70 | 8.26 |
| Traub-Johnson | 350 | 1.73 | 4.71 | 11.06 | 15.96 | 3.74 | 3.34 |
| Traub-Kichen | 344 | 1.16 | 4.79 | 10.04 | 16.43 | 3.68 | 3.27 |

TABLE 7b

Predictive performance of the Mercy method and other weight estimation methods on data collected from children enrolled in Pondicherry, India.

| | | ME | | MPE | | RMSE | |
|---|---|---|---|---|---|---|---|
| | n | Mean | Std. Dev. | Mean | Std. Dev | Mean | Std. Dev. |
| Mercy | 409 | −0.94 | 2.86 | −1.34 | 9.26 | 2.05 | 2.20 |
| APLS | 212 | 1.10 | 3.97 | 10.09 | 17.70 | 2.89 | 2.92 |

TABLE 7b-continued

Predictive performance of the Mercy method and other weight estimation methods on data collected from children enrolled in Pondicherry, India.

|  | n | ME Mean | ME Std. Dev. | MPE Mean | MPE Std. Dev | RMSE Mean | RMSE Std. Dev. |
|---|---|---|---|---|---|---|---|
| ARC | 388 | 3.07 | 5.88 | 13.80 | 18.77 | 4.99 | 4.38 |
| Argall | 212 | 4.56 | 4.75 | 26.33 | 24.46 | 5.27 | 3.95 |
| Best Guess | 329 | 7.85 | 6.64 | 36.34 | 24.54 | 8.26 | 6.13 |
| Broselow | 282 | 1.72 | 2.97 | 10.62 | 12.40 | 2.62 | 2.21 |
| Cattermole | 130 | −2.65 | 2.91 | −11.43 | 12.47 | 3.20 | 2.29 |
| Leffler | 212 | 3.10 | 3.17 | 22.86 | 19.47 | 3.65 | 2.52 |
| Luscombe-Owens | 212 | 5.56 | 4.75 | 32.80 | 24.24 | 6.03 | 4.14 |
| Nelson | 294 | 4.98 | 5.98 | 23.95 | 24.03 | 5.75 | 5.23 |
| Shann | 388 | 1.58 | 5.72 | 11.77 | 19.08 | 4.39 | 3.99 |
| Theron | 212 | 8.78 | 8.10 | 45.67 | 35.46 | 8.94 | 7.92 |
| Traub-Johnson | 388 | 2.60 | 5.13 | 11.60 | 14.45 | 4.23 | 3.90 |
| Traub-Kichen | 385 | 1.54 | 5.02 | 9.25 | 14.25 | 3.81 | 3.61 |

The Mercy method estimated weights within 10% of actual for the majority of children in the study (70%, 72%) as opposed to the other methods for which weight was predicted to within 10% of actual for a minority of the participating children (range 6-36%) (Tables 8a and 8b). As most of the published methods tend to perform poorly at the extremes of weight, the data from India were segregated by BMI percentile and the Mercy method examined independently for infants and children who were underweight, normal, overweight and obese. Advantageously, the Mercy method performed with comparable predictive power irrespective of BMI classification.

TABLE 8a

Cumulative percentage agreement between predicted weight and actual weight in the Cuttack dataset.

| | | percentage in agreement within: | | | | | | | | | |
|---|---|---|---|---|---|---|---|---|---|---|---|
|  | n | 22 | 30 | 40 | 50 | 60 | 70 | 80 | 90 | 100 | >100 |
| Mercy | 374 | 70 | 96 | 99 | 99 | 99 | 99 | 99 | 99 | 99 | 99.7 |
| APLS | 249 | 17 | 30 | 45 | 56 | 62 | 65 | 66 | 67 | 67 | 67 |
| ARC | 350 | 23 | 41 | 59 | 72 | 84 | 88 | 91 | 92 | 92 | 93 |
| Argall | 249 | 10 | 23 | 31 | 41 | 48 | 52 | 58 | 63 | 64 | 66 | 66 |
| Best Guess | 347 | 10 | 24 | 35 | 44 | 57 | 68 | 75 | 81 | 86 | 89 | 93 |
| Broselow | 321 | 28 | 60 | 79 | 84 | 85 | 85 | 85 | 85 | 85 | 86 | 86 |
| Cattermole | 151 | 15 | 27 | 35 | 38 | 39 | 40 | 40 | 40 | 40 | 40 | 40 |
| Leffler | 247 | 11 | 23 | 34 | 42 | 53 | 58 | 62 | 64 | 65 | 65 | 66 |
| Luscombe-Owens | 249 | 6 | 14 | 27 | 36 | 44 | 50 | 56 | 60 | 63 | 65 | 67 |
| Nelson | 329 | 18 | 31 | 45 | 57 | 68 | 73 | 79 | 82 | 85 | 86 | 88 |
| Shann | 350 | 22 | 42 | 55 | 73 | 83 | 88 | 91 | 92 | 93 | 94 | 94 |
| Theron | 249 | 7 | 14 | 23 | 31 | 38 | 41 | 45 | 50 | 54 | 58 | 66 |
| Traub-Johnson | 350 | 29 | 62 | 85 | 90 | 93 | 93 | 93 | 93 | 93 | 93 | 93 |
| Traub-Kichen | 344 | 28 | 63 | 84 | 89 | 91 | 92 | 92 | 92 | 92 | 92 | 92 |

TABLE 8b

Cumulative percentage agreement between predicted weight and actual weight in the Pondicherry data.

| | | percentage in agreement within: | | | | | | | | | |
|---|---|---|---|---|---|---|---|---|---|---|---|
|  | n | 10 | 20 | 30 | 40 | 50 | 60 | 70 | 80 | 90 | 100 | >100 |
| Mercy | 409 | 72 | 97 | 99 | 100 | | | | | | | |
| APLS | 212 | 19 | 36 | 45 | 48 | 51 | 52 | 52 | 52 | 52 | 52 | 52 |
| ARC | 388 | 30 | 58 | 75 | 85 | 93 | 94 | 95 | 95 | 95 | 95 | 95 |
| Argall | 212 | 10 | 19 | 29 | 38 | 43 | 47 | 49 | 51 | 52 | 52 | 52 |
| Best Guess | 329 | 12 | 20 | 34 | 49 | 58 | 65 | 72 | 78 | 79 | 80 | 81 |
| Broselow | 282 | 28 | 51 | 67 | 68 | 69 | 69 | 69 | 69 | 69 | 69 | 69 |
| Cattermole | 130 | 13 | 25 | 30 | 31 | 31 | 31 | 32 | 32 | 32 | 32 | 32 |
| Leffler | 212 | 10 | 24 | 34 | 43 | 47 | 50 | 51 | 52 | 52 | 52 | 52 |
| Luscombe-Owens | 212 | 8 | 14 | 24 | 34 | 39 | 45 | 48 | 51 | 52 | 52 | 52 |
| Nelson | 294 | 18 | 33 | 44 | 54 | 59 | 65 | 70 | 71 | 72 | 72 | 72 |
| Shann | 388 | 32 | 59 | 77 | 87 | 92 | 95 | 95 | 95 | 95 | 95 | 95 |
| Theron | 212 | 7 | 13 | 20 | 28 | 31 | 36 | 40 | 43 | 45 | 48 | 52 |
| Traub-Johnson | 388 | 33 | 66 | 87 | 93 | 94 | 95 | 95 | 95 | 95 | 95 | 95 |
| Traub-Kichen | 385 | 36 | 69 | 89 | 93 | 94 | 94 | 94 | 94 | 94 | 94 | 94 |

Overall, the Mercy method performed exceedingly well in the T.A.P.E.-India study. The predictive performance of the method in Indian children appears comparable to the performance of the method in U.S. children. Although data on height, arm span and other long bones were collected in anticipation of the need to develop an India-specific method, it does not appear that modification of the existing Mercy method is required for accurate weight estimation in Indian children.

Weight estimation strategies address a critical medical need in settings where there is neither the time nor the opportunity to directly weigh patients. To date, no single previous method has provided accurate estimates of weight across a broad range of ages, weights and lengths. The Mercy method attempts to address limitations inherent in the existing weight estimation strategies. It expands the age range of children to which a single weight estimation method can be applied and removes length restrictions observed in other commonly used methods. T.A.P.E.-India is the first prospective evaluation of the Mercy method in non-U.S. children. The results of this study suggest that the utility of Mercy method extends beyond the U.S.

What is claimed is:

1. A device for estimating weight in a child between the ages of 2 months to 16 years, said device comprising:
   a flexible elongate strip having a front side and a back side, each of said front side and said back side including a scale of indicia thereon;
   wherein said scale of indicia on said front side provides a first value when said flexible elongate strip is used to measure the circumference of a body part and said scale of indicia on said back side provides a second value when said flexible elongate strip is used to measure at least a portion of the length of a body part; and,
   wherein said first value and said second value are added together to estimate the weight of the child.

2. The device of claim 1, wherein said scale of indicia for said front side is derived for a circumference measurement of a body part selected from the group consisting of the upper arm, neck, abdomen, and upper leg.

3. The device of claim 1, wherein said scale of indicia for said back side is derived for a length measurement of at least a portion of a body part selected from the group consisting of the humerus, ulna, tibia, and femur.

4. The device of claim 3, wherein the length measurement is the length of the humerus.

5. The device of claim 1, wherein the body part used for the circumference measurement and the body part used for the length measurement are the same body part.

6. The device of claim 1, wherein said scale of indicia for said front side is in 1 cm gradations.

7. The device of claim 1, wherein said scale of indicia for said back side is in 1 cm gradations.

8. The device of claim 6, wherein said gradations on said scale of indicia for said front side are 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively.

9. The device of claim 7, wherein said gradations on said scale of indicia for said back side are 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively.

10. The device of claim 1, wherein said indicia on each said scale of indicia are in a form selected from the group consisting of numbers, letters, symbols, colors, and combinations thereof.

11. A device for estimating weight in a child between the ages of 2 months to 16 years, said device comprising:
    a first flexible elongate strip having a front side including a scale of indicia thereon and two opposed ends;
    a second flexible elongate strip having a front side including a scale of indicia thereon;
    wherein the two opposed ends of said first flexible elongate strip are slidably engaged with one another and wherein said first flexible elongate strip is attached to and oriented perpendicularly to said second flexible elongate strip;
    said scale of indicia on said first flexible elongate strip providing a first value when used to measure the circumference of a body part and said scale of indicia on said second elongate strip providing a second value when used to measure at least a portion of the length of a body part; and,
    wherein said first value and said second value are combined to estimate the weight of the child.

12. The device of claim 11, wherein said scale of indicia for said first flexible elongate strip is derived for a circumference measurement of a body part selected from the group consisting of the upper arm, neck, abdomen, and upper leg.

13. The device of claim 12, wherein the circumference measurement is taken at the midpoint of the humerus.

14. The device of claim 11, wherein said scale of indicia for said second flexible elongate strip is derived for a length measurement of at least a portion of a body part selected from the group consisting of the humerus, ulna, tibia, and femur.

15. The device of claim 14, wherein the length measurement is the half-length of the humerus.

16. The device of claim 11, wherein said scale of indicia for said first flexible elongate strip is in 1 cm gradations.

17. The device of claim 16, wherein said gradations on said scale of indicia for said first flexible elongate strip are 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively.

18. The device of claim 11, wherein said scale of indicia for said second flexible elongate strip is in 0.5 cm gradations.

19. The device of claim 18, wherein said gradations on said scale of indicia for said second flexible elongate strip are 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively.

20. The device of claim 11, wherein said indicia on each said scale of indicia are in a form selected from the group consisting of numbers, letters, symbols, colors, and combinations thereof.

21. A method of estimating the weight of a child between 2 months and 16 years of age, said method comprising the steps of:
    measuring the circumference of a first body part using a flexible elongate strip having a first scale of indicia thereon;
    measuring the length of at least a portion of a second body part using a flexible elongate strip having a second scale of indicia thereon;
    said first scale of indicia providing a first value when used to measure the circumference of a body part and said second scale of indicia providing a second value when used to measure at least a portion of the length of a body part; and,
    combining said first value and said second value to thereby estimate the weight of the child.

22. The method of claim 21, wherein said first scale of indicia and said second scale of indicia are on opposing sides of said flexible elongate strip.

23. The method of claim 21, wherein said first scale of indicia is on a first flexible elongate strip and said second scale of indicia is on a second flexible elongate strip.

24. The method of claim 23, wherein said first flexible elongate strip includes two opposing ends that are slidably engaged with one another and wherein said first flexible elongate strip is attached to and oriented perpendicularly to said second flexible elongate strip.

25. The method of claim 21, wherein said first scale of indicia is derived for a circumference measurement of a body part selected from the group consisting of the upper arm, neck, abdomen, and upper leg.

26. The method of claim 25, wherein the circumference measurement is taken at the midpoint of the humerus.

27. The method of claim 21, wherein said second scale of indicia is derived for a length measurement of at least a portion of a body part selected from the group consisting of the humerus, ulna, tibia, and femur.

28. The method of claim 27 wherein the length measurement is the length of the humerus.

29. The method of claim 21, wherein said first scale of indicia includes gradations 1 cm in length that are 2.8, 3.8, 4.6, 4.9, 5.3, 5.9, 6.5, 7.4, 8.0, 9.4, 10.9, 12.4, 14.3, 16.5, 18.0, 20.5, 23.4, 25.5, 27.8, 30.5, 33.3, 36.3, 39.6, 44.8, 46.5, 50.2, 53.2, 55.7, 60.3, 61.1, 67, 74, 75, 77, 80, 82, 84, and 96, respectively.

30. The method of claim 21, wherein said second scale of indicia includes gradations 0.5 cm in length that are 0.5, 0.7, 0.9, 1.5, 2, 2.8, 3.4, 4.2, 5.0, 6.1, 7.2, 8.1, 9.1, 10.4, 11.4, 12.6, 13.7, 14.7, 16.6, 18.3, 19.6, 21.4, 23.7, 25.5, 27.3, 29.2, 31.0, 33.5, 34.5, 36.5, 38.2, 40.0, 41.5, 43.0, 49.0, 50.0, and 53.0, respectively.

* * * * *